(12) United States Patent
Banerjee

(10) Patent No.: US 6,405,070 B1
(45) Date of Patent: *Jun. 11, 2002

(54) DETECTION OF CANCER USING CELLULAR AUTOFLUORESCENCE

(76) Inventor: Bhaskar Banerjee, 9631 Mansfield Dr., St. Louis, MO (US) 63132

(*) Notice: Subject to any disclaimer, the term of this patent is extended or adjusted under 35 U.S.C. 154(b) by 0 days.

This patent is subject to a terminal disclaimer.

(21) Appl. No.: 09/522,557

(22) Filed: Mar. 10, 2000

Related U.S. Application Data

(63) Continuation-in-part of application No. 09/097,931, filed on Jun. 16, 1998.

(51) Int. Cl.[7] ................................................ A61B 5/00
(52) U.S. Cl. ...................... 600/407; 600/477; 600/478; 436/64
(58) Field of Search ................................. 600/407, 473, 600/475–478, 310; 436/63, 64; 356/300, 301, 317, 318

(56) References Cited

U.S. PATENT DOCUMENTS

| | | | |
|---|---|---|---|
| 4,930,516 A | | 6/1990 | Alfano et al. |
| 5,042,494 A | | 8/1991 | Alfano |
| 5,131,398 A | | 7/1992 | Alfano et al. |
| 5,419,323 A | * | 5/1995 | Kittrell et al. ............... 600/407 |
| 5,504,337 A | | 4/1996 | Lakowicz et al. .......... 356/318 |
| 5,507,287 A | | 4/1996 | Palcic et al. |
| 5,769,081 A | * | 6/1998 | Alfano et al. ................ 600/476 |
| 5,784,162 A | | 7/1998 | Cabib et al. |
| 5,999,844 A | * | 12/1999 | Gombrich et al. .......... 600/476 |

OTHER PUBLICATIONS

Collins et al., Colon Cancer, Dysplasia, And Surveillance In Patients With Ulcerative Colitis, *The New England J. Med.* 316:1654–1658; Jun. 25, 1987.

Alfano et al., Fluorescence Spectra from Cancerous and Normal Human Breast and Lung Tissues, *IEEE Journal of Quantum Electronics* QE–23:1806–1811, Oct., 1987.

Kapadia, et al., Laser–Induced Fluorescence Spectroscopy of Human Colonic Mucosa, *Gastroenterology*: 99:150–157, Jul., 1990.

Cothren et al., Gastrointestinal Tissue Diagnosis by Laser–Induced Fluorescence Spectroscopy at Endoscopy, *Gastrointestinal Endoscopy*, 36:105–110, 1990.

Mahadevan et al., Study of the Fluorescence Properties of Normal and Neoplastic Human Cervical Tissue, *Lasers in Surgery and Medicine* 13:647–655, May 25, 1993.

Panjehpour et al., Spectroscopic Diagnosis of Esophageal Cancer: New Classification Model, Improved Measurement System, *Gastrointestinal Endoscopy*, 41:577–581, 1995.

Banerjee et al., Autofluorescence Spectral Band Distribution of Adenomatous Colon Polyps, *Am. J. Gastroenterology*, 91:1964, 1996.

Banerjee et al., Autofluorescence Spectroscopy Of Colon Cells and Polyps, *Diabetes Concurrent Session*, Sep. 20, 1996.

(List continued on next page.)

*Primary Examiner*—Ruth S. Smith
(74) *Attorney, Agent, or Firm*—Harness, Dickey, & Pierce, P.L.C.

(57) ABSTRACT

Apparatus and methods especially useful for detection of cancer using cellular, Tryptophan-associated autofluorescence are described. The apparatus includes a light source to produce a beam of light transmitted to a tissue via a two-way fiber optic bundle which, in one embodiment, is passed through a conventional endoscope. The light beam excites the tissue, resulting in an emission of primarily cellular autofluorescence at a wavelength of about 330 nm. Light from the tissue is directed back through the fiber optic bundle and passes through a photodetector. The photodetector produces a signal, representative of the intensity of the Tryptophan-associated autofluorescence.

11 Claims, 11 Drawing Sheets

OTHER PUBLICATIONS

Banerjee et al., Autofluorescence Spectroscopy of Colon Cells and Polyps, *Am. J. Gastroenterology*, 91:1964, 1996.

Banerjee et al., Emission Spectra of Colonic Tissue and Endogenous Fluorophores, *Am. J. Med. Science* 316:220–226; Sep., 1998.

Heintzelman et al., Characterization of the Autofluorescence of Polymorphonuclear Leukocytes, Mononuclear Leukocytes and Cervical Epithelial Cancer Cells for Improved Spectroscopic Discrimination of Inflammation from Dysplasia, *Photochemistry and Photobiology* 71:327–332; Mar. 16, 2000.

* cited by examiner

DETECTION OF CANCER USING CELLULAR AUTOFLUORESCENCE

This application is a continuation-in-part application of prior application Ser. No. 09/097,931, filed Jun. 16, 1998, and incorporated herein by reference.

BACKGROUND OF THE INVENTION

This invention relates generally to detection of cancerous cells and more particularly, to detecting cancerous cells using cellular autofluorescence.

The survival rate for cancer patients increases with early detection of cancer. Known methods of gaining early detection of cancer are limited to techniques such as surveillance endoscopy and random tissue biopsies, both of which are costly and inefficient. In addition, methods which employ relatively high levels of radiation which cause tissue damage generally are not preferred. Autofluorescence has been used in attempts to detect cancerous tissue. Particularly, fluorescence occurs when certain substances called fluorophores emit light of a longer wavelength after being excited by light of another, shorter wavelength. The fluorescence which occurs in human and animal tissues is commonly referred to as autofluorescence because the fluorescence results from fluorophores occurring naturally in the tissues. The intensity of autofluorescence differs in normal and cancerous tissues, and autofluorescence can be used to detect cancerous tissue in different organs, including the colon, esophagus, breast, skin, and cervix.

In many medical and laboratory applications, the use of autofluorescence often is preferred for detecting cancerous tissue because autofluorescence avoids the introduction of exogenous fluorophores or any other exogenous agent. The use of exogenous agents increases costs and results in time delays due to lag in incorporating the exogenous agents into the examined tissue. Exogenous agents also introduce the risk of adverse reaction.

Known work on the use of autofluorescence to detect cancer has been limited to examinations of whole tissue in which a decrease in tissue autofluorescence indicates the presence of cancer. However, such work is limited because it relies on measurement of autofluorescence which includes in large part non-specific autofluorescence which is emitted from certain but varied extracellular components of whole tissue. Such extracellular components include blood, blood vessels, collagen and elastin, which all emit autofluorescence. While these extracellular components may change during the progression from normal to cancerous tissue, the changes are not specific to the cells which constitute the actual cancerous tissue. Thus, known uses of autofluorescence to detect cancerous tissue cannot distinguish between specifically cellular changes and non-specific extracellular changes in the progression from normal to cancerous tissue.

It would therefore be desirable to provide apparatus and methods which facilitate the early detection of cancerous cells using autofluorescence. It would also be desirable to provide such autofluorescence apparatus and methods which exclude extracellular changes which are non-specific to cancer. It would further be desirable to provide an objective method for early detection of cancer which is simple to practice and avoids the need for complex, subjective comparisons. It would be yet still further desirable to provide a method for the early detection of cancer which exhibits a reliability which is unaffected by tissue inflammation.

SUMMARY OF THE INVENTION

These and other objects may be attained by apparatus and methods for measuring cellular, Tryptophan-associated autofluorescence to enable the early detection of cancerous cells. In one embodiment, the apparatus includes a light source for producing a beam of light to excite a tissue to emit cellular autofluorescence. The beam of light is first filtered through a narrow-band optical filter configured to pass light at a wavelength of about 200 to about 400 nm, which is optimal for producing cellular autofluorescence. The beam of light is then transmitted to the tissue via a two-way fiber optic bundle having a sampling end positioned at or near the tissue being examined. A lens-system is positioned between the sampling end of the two-way fiber optic bundle and the tissue, and the lens system is configured to collect a light sample from the tissue. The light sample is transmitted back through the two-way fiber optic bundle and passes through a narrow-band optical filter configured, in one embodiment, to pass light at wavelengths of about 320–340 nm. A photodetector positioned at the output end of the two-way fiber optic bundle measures the intensity of cellular autofluorescence emitted from the tissue.

In another aspect the present invention relates to a method for detecting pre-cancerous and cancerous cells in a tissue and in one embodiment, the method includes the steps of exciting the tissue with a beam of light delivered through a two-way fiber optic bundle, and measuring the intensity of cellular Tryptopan-associated autofluorescence emitted from the tissue. The two-way fiber optic bundle may be inserted through the biopsy channel of an endoscope, through a laparoscope, or through a needle inserted into the tissue. The light beam has a wavelength of about 200 to about 400 nm, and the light sample is transmitted back through the two-way fiber optic bundle and through a narrow-band optical filter configured to pass light at wavelengths of about 300–400 nm. In an exemplary embodiment the optical filter is configured to pass light at wavelengths of about 320–340 nm, and a filter passing light at wavelengths of about 330 nm is especially suitable.

Measuring the intensity of the light sample at an emission wavelength of about 300–400 nm, and particularly at about 330 nm, enables detection of pre-cancerous and cancerous cells. Specifically, the intensity of the light sample at about 330 nm increases systematically with the progression of cancer from normal to cancerous tissue. Although Tryptophan is believed to be present in some extracellular proteins, it is predominantly present in cells. It is believed that the cell specific fluorescence originates from membranous cellular structures which contain the amino acid Tryptophan. Thus, at the wavelengths identified above, extracellular changes which are non-specific to cancer are largely excluded and therefore, primarily the cellular changes are detected.

DETAILED DESCRIPTION OF THE INVENTION

The present invention is directed to apparatus and methods for detecting cancer in vitro and in vivo using cellular autofluorescence. Although specific embodiments of the apparatus and methods are described below, many variations and alternatives are possible. Also, the term tissue as used herein refers to. both in vitro and in vivo tissues. In addition, the term tissue as used herein refers to tissue, organs (in vivo or in live animals or humans), as well as samples of cells, such as in cytology (examination of a film of cells on a glass slide). Further, the cancer detection apparatus and methods can be used in connection with the detection of early cancer, or pre-cancer, or dysplasia.

Figure 1:
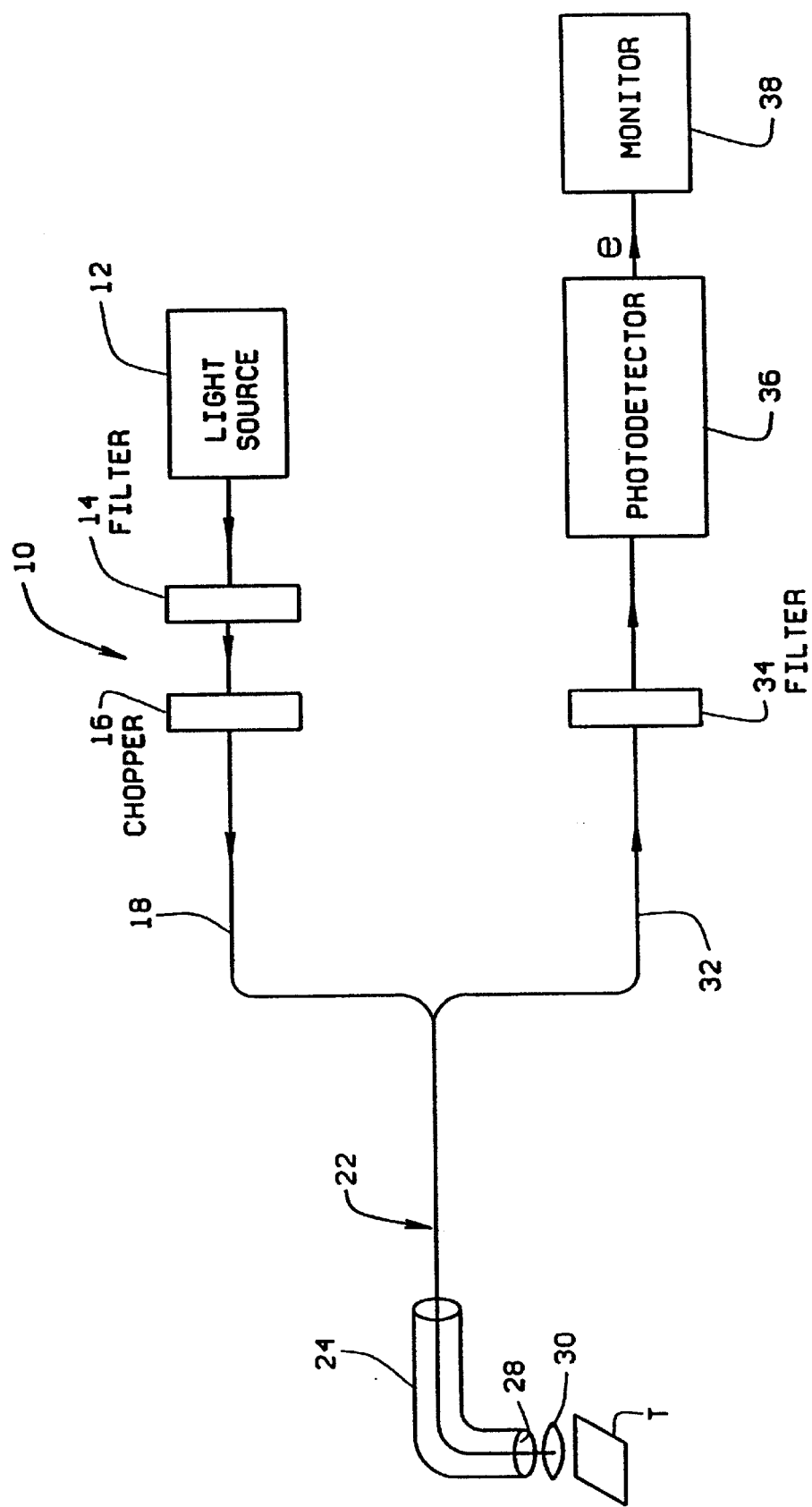
FIG. 1 is a schematic illustration of an apparatus for detection of cancer using cellular autofluorescence in accordance with one embodiment of the present invention.

Referring specifically to the drawings, FIG. 1 is a schematic view of an apparatus 10 for detecting cancer in vitro or in vivo using cellular autofluorescence. Apparatus 10 includes a light source 12, such as a Xenon arc lamp or a laser, powered by a conventional power source. A first optical filter 14 with a narrow bandwidth of about 10 nm to about 50 nm, configured to pass light at a wavelength in a range of about 200 to about 400 nm is positioned in the path of the light beam produced by light source 12. In an exemplary embodiment, first optical filter 14 has a narrow bandwidth of about 10 nm and is configured to pass light at a wavelength in a range of about 270–310 nm. In an alternative embodiment, first optical filter 14 has a band width of about 35 nm. The light beam emerging from first optical filter 14 passes through an optical chopper 16 which removes wavelengths of any background light. The light beam then passes through a two-way fiber optic bundle 22, sometimes referred to herein as a probe, which is positioned to catch the light beam as it emerges from optical chopper 16. The two-way fiber optic bundle 22 has a sampling end 28, and comprises two groups of optic fibers. A first group of optic fibers 18 transmits light from source of light 12 to a tissue T. A second group of optic fibers 32 transmits a light sample back from tissue T for analysis.

The two optical fiber groups of two-way fiber optic probe 22 are intermeshed. Two-way fiber optic probe 22 is less than about 2.5 mm in diameter and is long enough to pass through the biopsy channel of an endoscope or laparoscope, e.g., about 1–2 m in length. Specifically, probe 22 is configured to pass through the biopsy channel of a conventional endoscope 24, such as the endoscopes commonly used to examine the gastrointestinal tract or the lungs. In an alternate embodiment, two-way fiber optic bundle 22 may be passed through a needle or trocar to obtain measurements of cellular autofluorescence intensity from solid masses or organs such as breast, liver or pancreas.

In one embodiment, a lens system 30 is positioned between sampling end 28 of two-way fiber optic bundle 22 and tissue T. Lens system 30 is provided to avoid direct contact between the tissue and probe 22. Light emerging from tissue T, including emissions of cellular autofluorescence and reflected and scattered light, is transmitted down fiber optic bundle 22 and collected by lens system 30 to form a light sample. In an alternative embodiment, probe 22 does not include a lens system and probe 22 makes direct contact with the tissue. The light emerging from tissue T is transmitted down fiber optic bundle 22.

The light sample is directed to sampling end 28 of two-way fiber optic bundle 22. The light sample is then transmitted back through two-way fiber optic bundle 22, along second group of optic fibers 32, from sampling end 28 to a second optical filter 34. In one embodiment, second optical filter 34 has a narrow bandwidth of about 20 nm, configured to pass light at a wavelength of about 320 to about 340 nm, and is positioned in the path of the light sample transmitted back from tissue T. In an alternative embodiment, optical filter 34 is configured to pass light at a wavelength of about 330 nm. In another embodiment, optical filter 34 has a broader bandwidth and passes light at wavelengths of about 300 to 400 nm. A photodetector 36 is positioned to collect the light sample as it emerges from second optical filter 34. Photodetector 36 is configured to measure the intensity of the light sample across wavelengths varying from about 300 nm to about 400 nm. In an alternative exemplary embodiment, photodetector 36 is configured to measure the intensity of the light sample across wavelengths varying from about 320 nm to about 340 nm.

Photodetector 36 generates an electrical output signal e whose magnitude is proportional to the intensity of the light sample at a wavelength of about 330 nm. Electrical output signal e is amplified and displayed on a monitor 38 as a wave form or meter response. The intensity of cellular autofluorescence in tissue T may thus be noted and compared to the intensity of cellular autofluorescence at about 330 nm in a tissue whose condition is known, such as a cancerous. pre-cancerous or normal tissue. The presence of cancerous cells is indicated by an increase, relative to normal tissue, in intensity of cellular autofluorescence at an emission wavelength of about 330 nm. A ratio of the intensity of cellular autofluorescence in the tissue $F_1$ to the intensity of cellular autofluorescence in a known normal sample $F_n$ may be constructed. The greater the value of $F_1/F_n$, the more severe the degree of cancer or malignancy.

Figure 2:
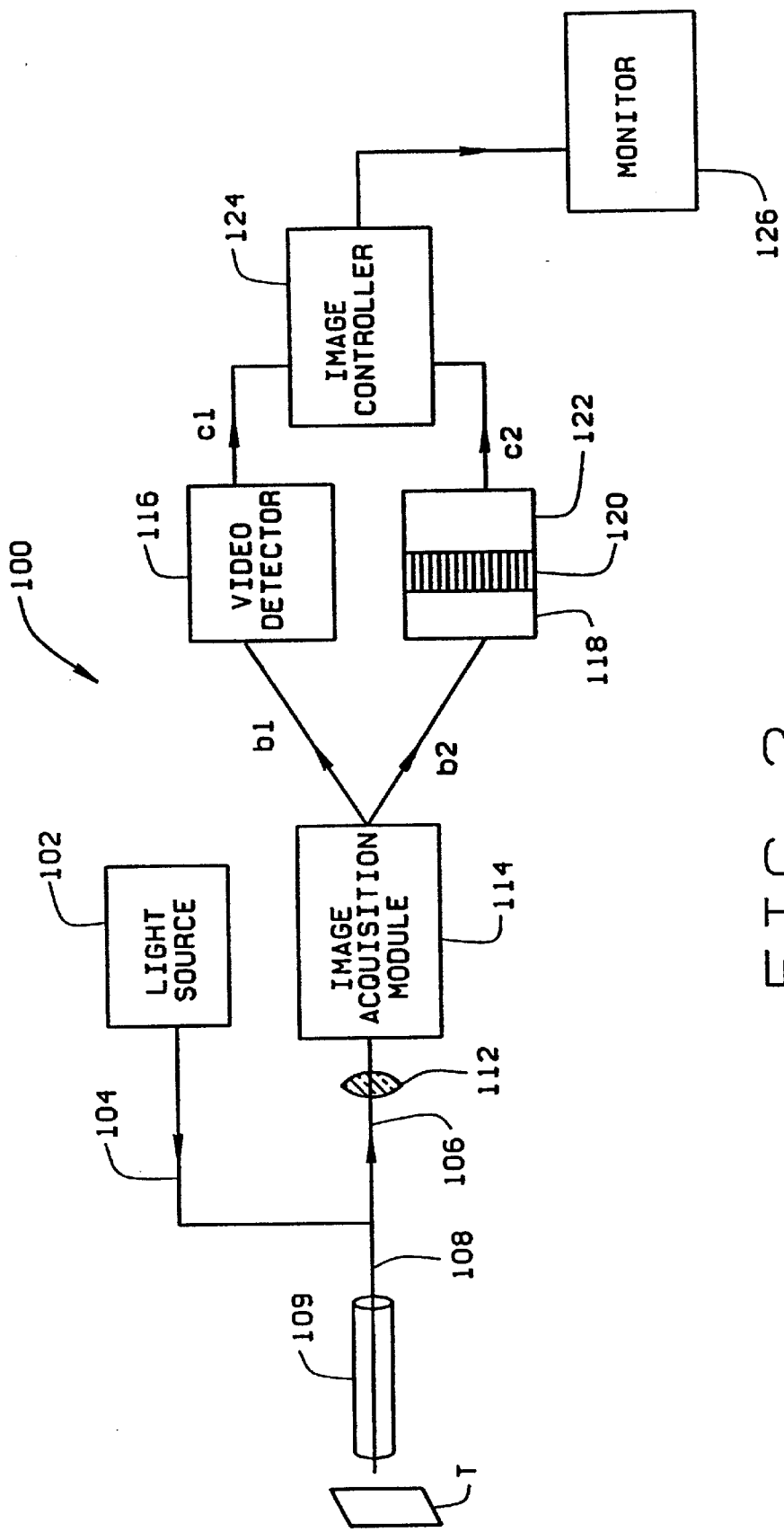
FIG. 2 is a schematic illustration of an apparatus for detection of cancer using cellular autofluorescence in accordance with another embodiment of the present invention.

FIG. 2 is a schematic view of an apparatus 100 for real time detection of cancer in vitro or in vivo using cellular autofluorescence and video imaging technology. Apparatus 100 includes a source of white light 102, such as a Xenon arc lamp or a laser, is powered by a conventional power source and produces a beam of light. The light beam then passes through a first group of optic fibers 104 of a two-way fiber optic bundle 108 which is positioned to catch the light beam as it emerges from white light source 102. The first group of optic fibers 104 transmits the light beam to a tissue T. Two-way optic fiber bundle 108 passes through a conventional endoscope 109. In alternate embodiments, the two-way fiber optic bundle may pass through a large-bore needle, trocar or laparoscope. A lens system 110 is part of the endoscope 109 and interposed between tissue T and two-way fiber optic bundle 108. It is positioned to catch reflected and scattered light from tissue T, as well as emissions of cellular autofluorescence, to form a light sample from tissue T. A second group of optic fibers 106 in two-way fiber optic bundle 108 transmits the light sample back from tissue T.

The light sample transmitted along second group of optic fibers 106 of two-way fiber optic bundle 108 is directed into an image acquisition module. 114 by a lens 112. Image acquisition module 114 uses a standard optical device such as a prism or dichromatic mirror to split the light sample into two beams of light $b_1$ and $b_2$, each comprising identical wavelengths. Light beam b1 is transmitted to a conventional video detector 116 which produces a video signal c1 representative of the standard visual image obtained from tissue T with endoscope 109 and lens system 110. Light beam b2 is transmitted to an optical filter 118 with a bandwidth of about 20 nm at about 330 nm. Light beam b2 then impinges on an image intensifier 120, and then a charge-coupled device or CCD 122 which produces a second video signal c2. Video signal c2 is representative of the intensity of cellular autofluorescence emitted from tissue T. Video signal c2 is color-coded according to the intensity of cellular autofluorescence to visually represent different stages of malignancy of the lesion. Video signals c1 and c2 are then directed via conventional cable means to a computerized image controller 124 which combines the two video signals c1 and c2 into a single signal which represents the superimposition of the image represented by c2 onto the image represented by c1. The combined signal is then directed to a standard color video monitor 126 for display of the combined images.

Figure 3:
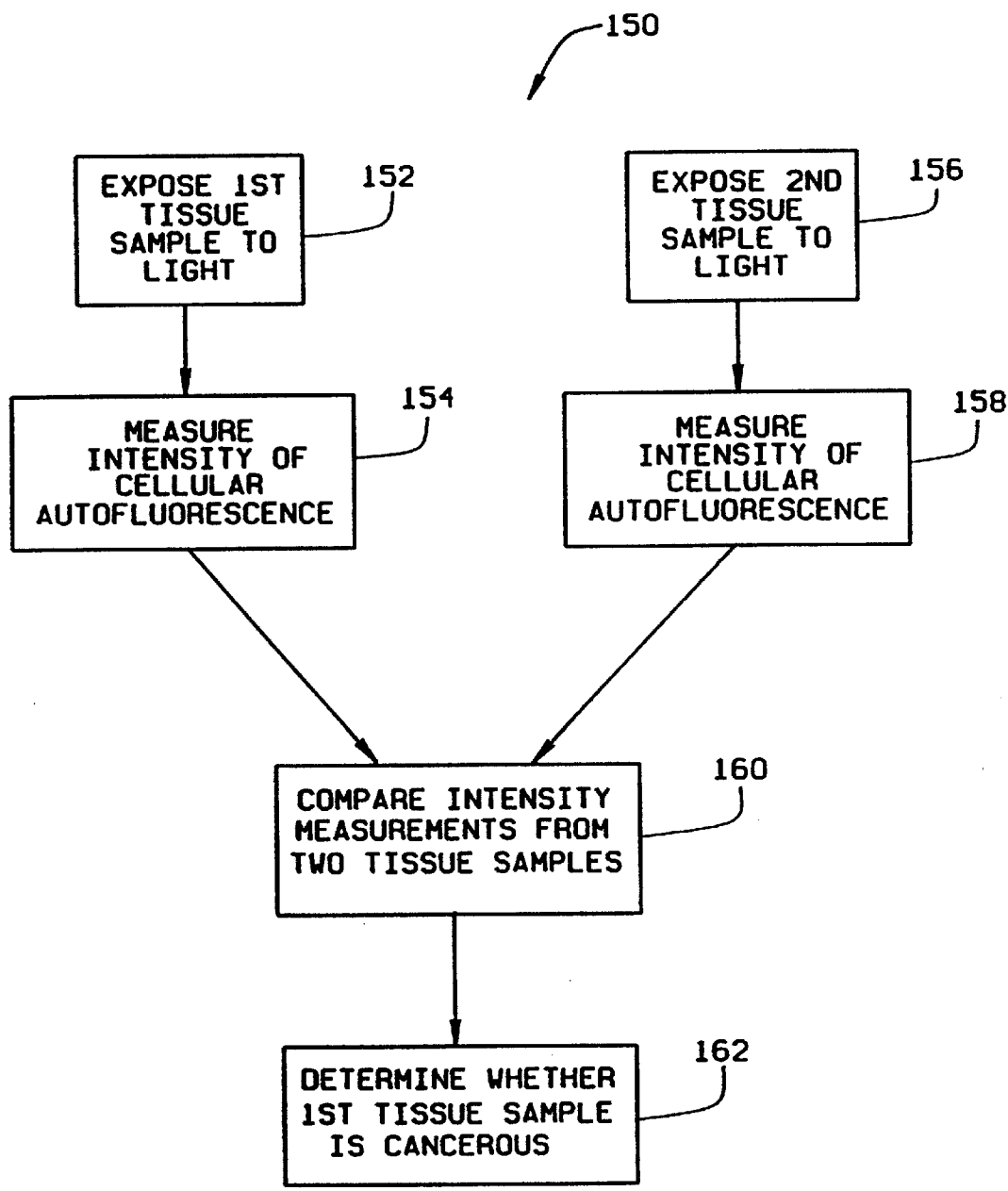
FIG. 3 is a flow chart illustrating a method for detection of cancer using cellular autofluorescence in accordance with an embodiment of the present invention.

FIG. 3 is a flow chart illustrating a method 150 for utilizing autofluorescence to detect dysplasia, early cancer and cancer. Method 150 includes exposing a first tissue to a light beam 152 which excites the tissue and results in an emission of cellular autofluorescence at a wavelength of about 330 nm. In this embodiment, the first tissue is being examined for the detection of cancer. After exposure of the tissue to the beam of light, the intensity of cellular autofluorescence emitted from the tissue is measured, at a wavelength of about 330 nm, using a standard photodetector 154.

In parallel, or in series, with steps 152 and 154, a second tissue whose condition is known as normal, pre-cancerous, or cancerous also is examined. Particularly, the second tissue is exposed to a light beam 156 which excites the tissue and results in an emission of cellular autofluorescence at a wavelength of about 330 nm. After exposure of the tissue to the beam of light, the intensity of cellular autofluorescence emitted from the tissue is measured, at a wavelength of about 330 nm, using a standard photodetector 158.

The intensity measurements from the first and second tissues are then compared 160. The intensity measurements obtained from the second tissue, which is of known condition, serves as a standard. Using the results of the comparison, the condition of the first tissue can be determined 162.

Method 150 may be practiced in vivo using a two-way fiber optic bundle passed through the biopsy channel of a conventional endoscope, as described above in connection with FIGS. 1 and 2. Alternatively, the first and second tissues may be collected tissue samples and method 150 may be practiced in a laboratory. In addition, method 150 could be practiced in connection with the use of a charge-coupled device and video imaging equipment. With such devices and equipment, and at steps 154 and 158, the intensity of the autofluorescence could be visually represented in a real time video image. Real time video scanning of cellular autofluorescence would allow large areas of tissue to be scanned both in vitro and in vivo. In alternative embodiments, method 150 is practiced on samples of cells obtained from brushings or aspirations.

Figure 4:
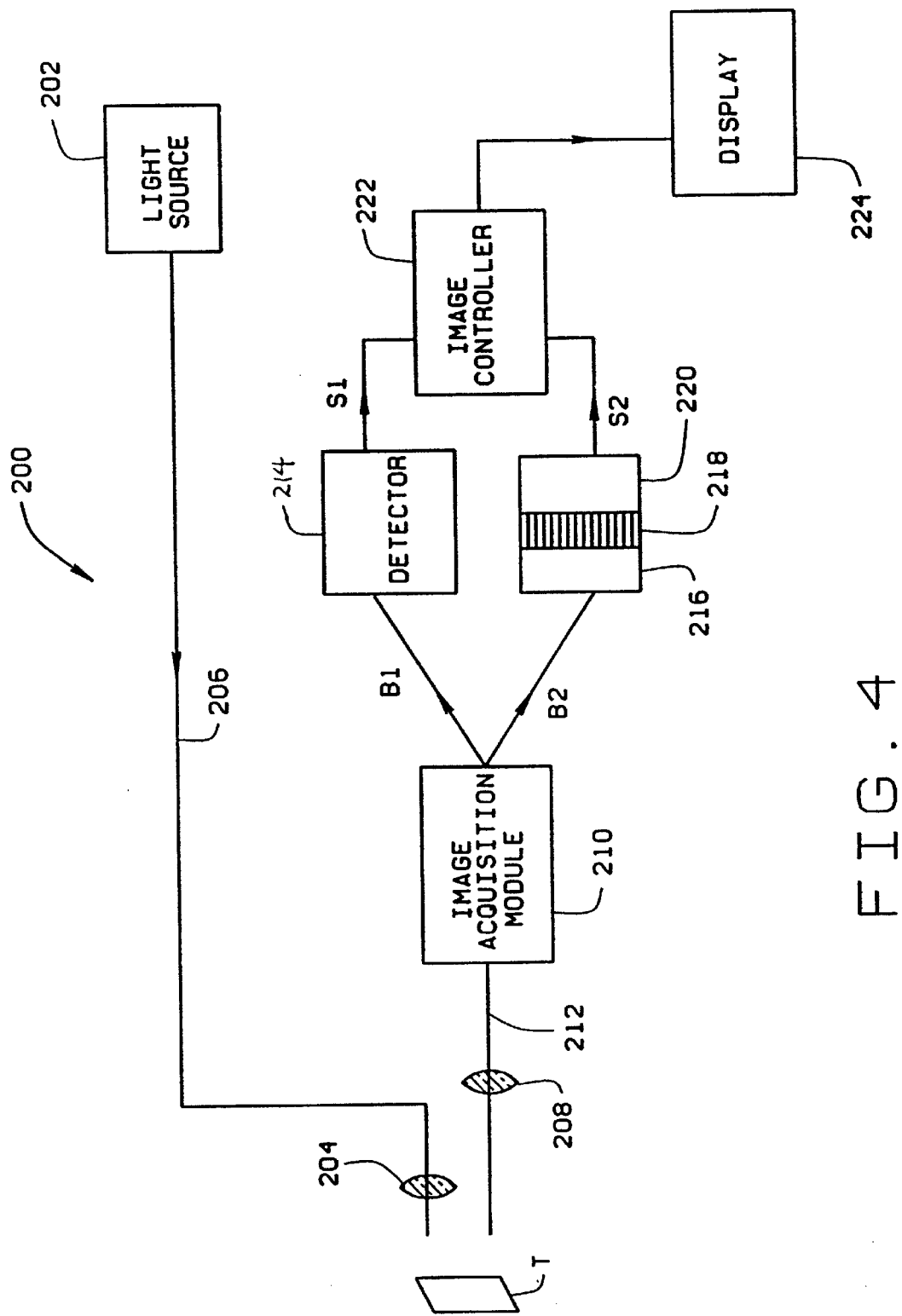
FIG. 4 is a schematic illustration of an apparatus for detection of cancer using cellular autofluorescence in accordance with yet another embodiment of the present invention.

FIG. 4 is a schematic illustration of an apparatus 200 for detection of cancer using cellular autofluorescence in accordance with yet another embodiment of the present invention. Apparatus 200 includes a light source 202 which may be a component of a conventional endoscopic illumination system. Light source is, for example, a Xenon lamp, a source of laser energy or other light source. Source 202 is coupled to a lens system 204 by a optical fiber bundle 206. Lens system 204 is focused on a tissue T, such as a tissue, a tissue sample, an organ, or cells. A lens system 208 is positioned to collect light from tissue T, and lens system 208 is coupled to an image acquisition module 210 by an optical fiber bundle 212. At image module 210, the light received from bundle 212 is split using a splitter such as a dichromatic mirror or a prism to produce two identical beams B1 and B2.

Light beam B1 is transmitted to a conventional video detector 214 which produces a video signal S1 representative of the standard visual image obtained from tissue T. Light beam B2 is transmitted to an optical filter 216 with a narrow band width of about 20 nm which allows wavelengths in the range of about 300 to about 400 nm to pass through. In one embodiment, optical filter 216 allows wavelengths in the range of about 320 nm to about 340 nm to pass through. Especially suitable are for optical filter 216 are optical filters having a narrow band width and allowing primarily wavelengths of about 330 nm to pass through. While a whole range of other, broader band filters can be used, narrow band filters maximize the signal. Light beam B2 then impinges on an image intensifier 218, and then a charge-coupled device or CCD 220 which produces a second video signal S2. Video signal S2 is representative of the intensity of cellular autofluorescence emitted from tissue T.

Signals S1 and S2 are supplied to a computerized image controller 222 coupled to a display 224. The autofluorescence image from signal S2 could be color coded (i.e., different colors represent different grades of fluorescence intensities, and hence stages of malignancy) and superimposed on the standard endoscopic image from signal S1. The intensity of cellular fluorescence would be stronger in malignant tissues than in normal tissue of the same organ, for example. The intensity of malignant areas also would be greater than that in dysplastic areas, which should be stronger than that in normal areas. If a laser source is used as light source 202, a gating mechanism could be utilized to rapidly and alternately illuminate the sample with white light (for routine video endoscopy) and the laser (for fluorescence imaging).

Without being bound to a particular theory, experimental evidence supports the theory that the cell specific fluorescence originates from proteins or other molecules which are present largely in membranous structures in cells and contain the amino acid Tryptophan. The intensity of autofluorescence from Tryptophan alone appears to be directly correlated to cellular changes associated with cancer, early (pre-) cancer or dysplasia. A stepwise increase in Tryptophan-induced autofluorescence is observed when normal tissue progresses to pre-cancer and cancer. Experiments using established techniques and standard equipment establish this correlation and are described below.

All fluorescence scans were performed using a spectrofluorometer from Shimatzu Inc., Columbia, Md., with a Xenon lamp and two spectrometers. Emission scans were performed with excitation from 230–350 nm, at 10 nm intervals. The autofluorescence intensity was measured in arbitrary units at 1 nm increments, from 10 nm above the excitation wavelength to 10 less than twice the excitation wavelength. The excitation scans were performed with emission at 350 nm and 400 nm, with excitation from 220 nm to 10 nm less than the emission wavelength.

EXAMPLE 1

The autofluorescence of whole tissue samples was studied. More specifically, samples of normal, dysplastic and malignant colonic tissue were studied. The tissue samples included hyperplastic and adenomatous polyps of the colon, and paired tissue samples from colon, each pair including a sample of normal mucosa and a sample of adenocarcinoma or polyp from the same colon. All tissue samples were immediately frozen in liquid Nitrogen and stored at −70° C. after harvesting. Just prior to spectroscopy, the tissue sample was thawed at room temperature and moistened with phosphate buffered saline (PBS) at a pH of 7.4. Solid tissue of similar shape and size was mounted on a specially constructed sample holder having a black matte surface and placed inside the spectrofluorometer. Spectra from the tissue samples were digitally recorded and later compared to spectra obtained from cells.

Figure 5:
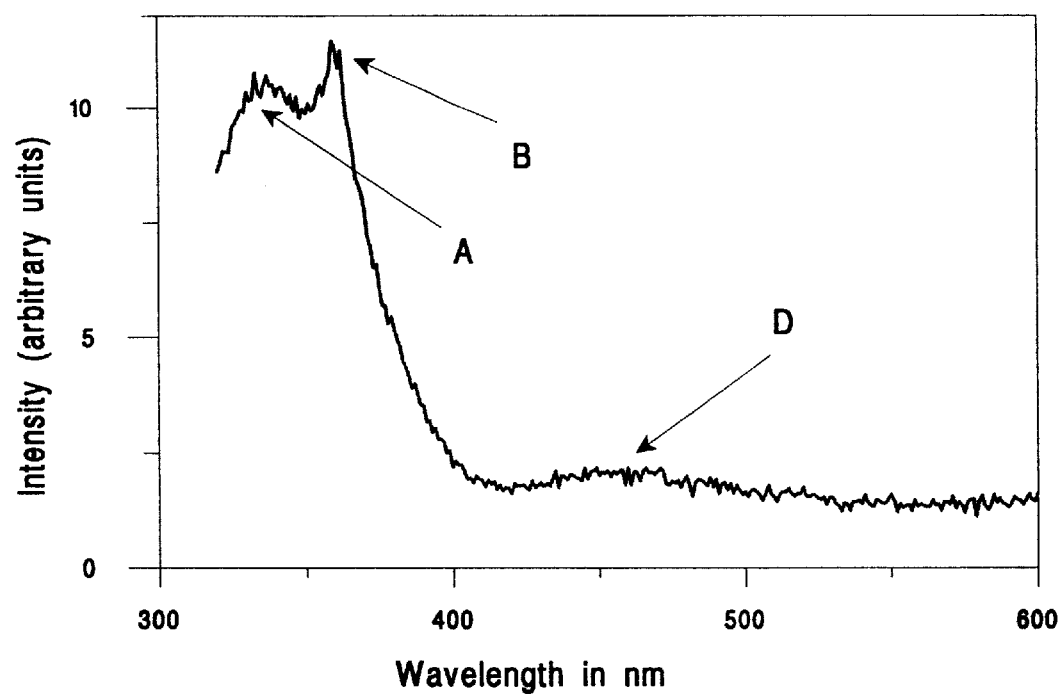
FIG. 5 is an exemplary autofluorescence emission spectrum of a tissue sample.

Emission spectra obtained from adenocarcinoma, polyps of the colon (both hyperplastic and adenomatous), and normal colon tissue samples revealed four major emission peaks or maxima, one at about 330 nm (A), one at about 365 nm (B), one at about 385 nm (C), and one at about 450 nm (D). FIG. 5 shows an exemplary emission spectrum, from an adenomatous polyp with excitation at 310 nm. Three of the four major emission peaks A–D were observed, at 330 nm (A), 365 nm (B), and 450 nm (D). Different emission peaks appeared as the excitation wavelength was varied, but the four major emission peaks A–D were observed across the range of excitation wavelengths studied. Esophageal, gastric and small intestinal tissue gave similar results. Peak A will be discussed in more detail below. As also will be discussed in more detail below, at least the relatively broad peak D at about 450 nm is likely to be of extracellular origin and therefore not indicative of the cell-specific changes associated with the development of cancer from normal tissue.

Table 1 summarizes the distribution of the major emission maxima A–D for normal (n), adenomatous (a) and cancerous (t) colonic tissue. Table 1 lists the mean wavelength, with standard error (SE), and the range of wavelengths at which each maximum occurred in each tissue type. A one way analysis of variance (ANOVA) was performed on the wavelength distribution of each maximum for each tissue type (e.g. $A_n$, $A_a$, and $A_t$), giving the P values as listed in Table 1. For normal tissue samples, N=20; for adenomatous polyps, N=20; for malignant tissue, N=20.

TABLE 1

| Maxima | Tissue type | Mean Wavelength | SE | P value | Range (nm) |
|---|---|---|---|---|---|
| A | n | 331.7 | 0.5 | 0.857 | 328–336 |
|   | a | 331.8 | 0.5 |       | 329–336 |
|   | t | 331.4 | 0.6 |       | 326–336 |
| B | n | 365.9 | 0.6 | 0.303 | 360–370 |
|   | a | 365.1 | 0.6 |       | 360–370 |
|   | t | 364.7 | 0.5 |       | 361–368 |
| C | n | 385.4 | 1.0 | 0.463 | 380–391 |
|   | a | 385.3 | 0.8 |       | 380–390 |
|   | t | 386.6 | 0.6 |       | 384–392 |
| D | n | 454.5 | 1.5 | 0.472 | 442–460 |
|   | a | 452.1 | 1.4 |       | 443–463 |
|   | t | 452.9 | 1.3 |       | 448–463 |

EXAMPLE 2

Cell specific autofluorescence was studied in cultured cells. Specifically, cultured cells were grown to isolate cell-specific autofluorescence from tissue autofluorescence which includes several nonspecific, extracellular sources such as, for example, collagen and elastin among others. Cultured cells do not contain any extracellular matrix. Cells derived from human colon adenocarcinoma (HT29-18N2) were grown on glass coverslips, in single and multi-layers until seen to be confluent. Cells were washed in PBS prior to spectroscopy to remove growth media.

Figure 6:
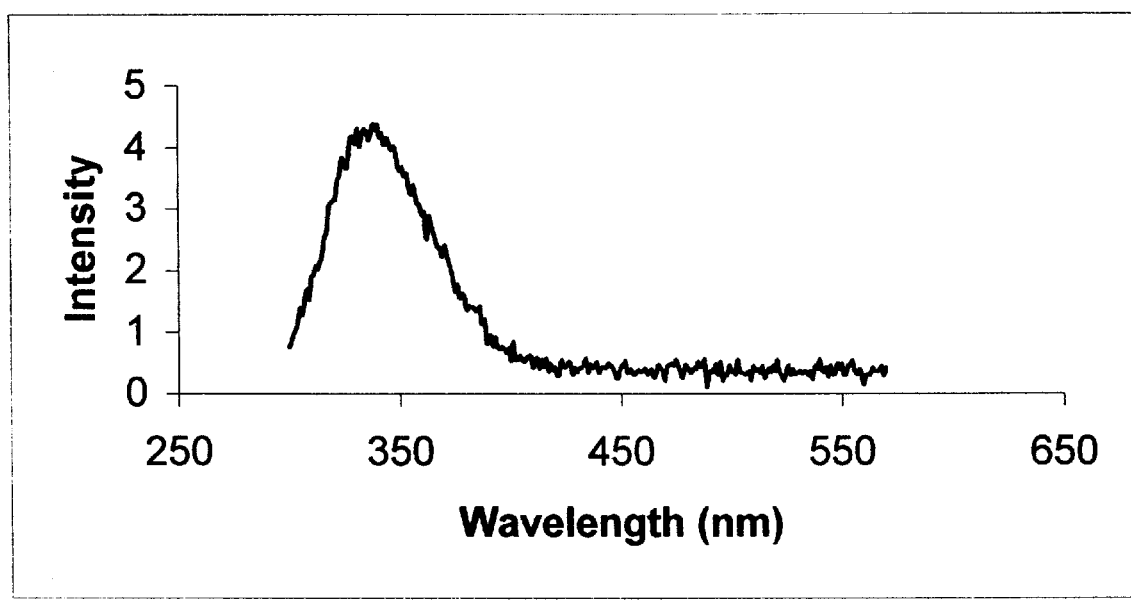
FIG. 6 is an emission spectrum of cultured cells.

FIG. 6 shows the emission spectrum of a monolayer of human colon adenocarcinoma (HT29-18N2) cells. Excitation of the cultured cells from 280 nm to 330 nm revealed only one major peak S at about 330 nm. Despite excitation at numerous wavelengths, S was the only major peak observed across the range from 280 nm to 700 nm. Thus S, a cellular autofluorescence peak, coincided with peak A, a major tissue autofluorescence peak as shown in FIG. 5. A similar peak at about 330 nm was observed in another cell culture derived from human breast tissue (MCF7). No peaks were observed in cells to match peaks B–D as described in Example 1 and FIG. 5 above.

To see if any other emission maxima might be present under different excitation wavelengths, excitation scans measuring light absorption at different wavelengths were performed. The excitation scans revealed maxima, or strongest absorption of light at 240 nm and 290 nm. Excitation of the cells from 235 nm to 270 nm revealed the S peak at about 330 nm, and an ill defined emission at 260 nm. However, because such low excitation wavelengths are potentially harmful, the 260 nm emission was not studied further. Excitation of the cells at the higher wavelength of 290 nm again revealed only the S peak.

All cultured cells, as well as cells separated from normal and malignant solid tissue including human colon, esophagus and stomach, which were studied at an excitation of 290 nm showed the S peak. No other emission peaks were seen.

Previously, it has been proposed that the broad D peak observed in tissue spectra at about 450 nm is due to the molecule NADH which is present in cells. However, none of the autofluorescence spectra from the cultured or extracted cells studied showed an emission peak matching D, thus indicating that the D fluorescence peak is not due to a cellular source.

EXAMPLE 3

Figure 7:
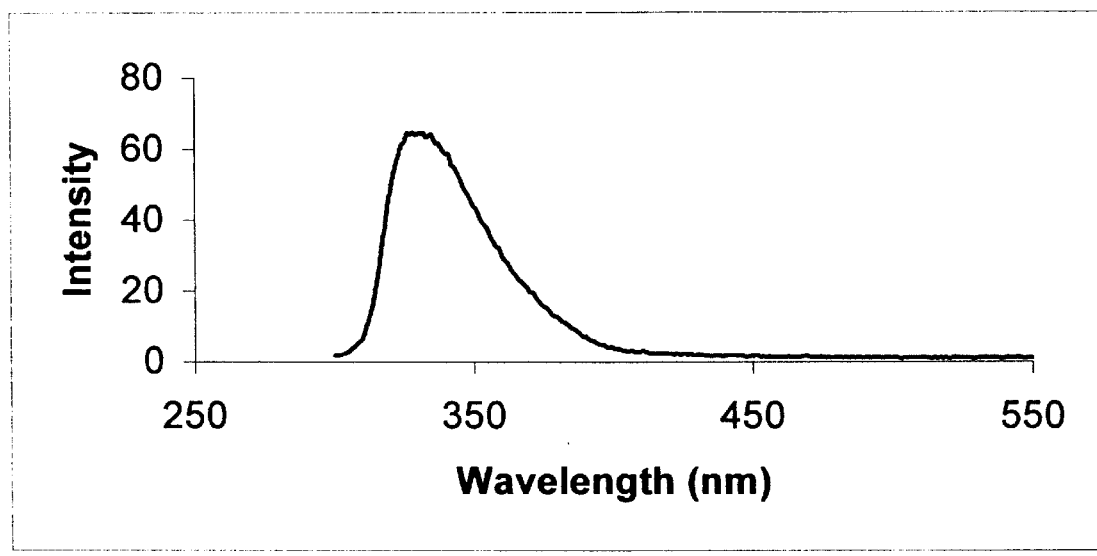
FIG. 7 is an emission spectrum of Tryptophan in aqueous solution.

To identify the origin of the S peak, the emission and excitation spectra of several known fluorophores were investigated at an excitation wavelength of 290 nm. The fluorophores included Phenylalanine, Tryptophan, Tyrosine, Collagen Type IV, Elastin, NADH, and FAD. Only the spectrum of Tryptophan, in aqueous solution, produced a peak matching the cellular autofluorescence S peak at about 330 nm, and the tissue autofluorescence peak A at about 330 nm. FIG. 7 shows the emission spectrum of Tryptophan in aqueous solution, at an excitation wavelength of 290 nm. Thus, Tryptophan is highly likely to be the predominant source of the cellular autofluorescence S peak and matching tissue autofluorescence A peak.

Further, the emission spectrum of NADH (not shown) showed a peak at 460 nm, not 450 nm. These results further support the idea that the broad D peak observed in tissue spectra at about 450 nm is not likely to be due to NADH. Thus, known methods which use the broad D peak to detect cancer are based on the likely false assumption that the D peak is correlated with the cellular marker NADH. Instead, the D peak is likely to be of extracellular origin and thus non-specific to the cellular changes associated with cancer. Further, the magnitude of peak D appears to fall with malignancy, probably due to a higher ratio of cells to extracellular tissue in cancer.

EXAMPLE 4

To demonstrate that increased autofluorescence at about 330 nm in cancerous cells is due to intracellular changes and not explained by greater cell density in cancerous tissue, cell samples were prepared and studied. Specifically, cells were separated from the extracellular matrix of normal and malignant tissue from colon and other organs. Cells separated from tissue and suspended in non-fluorescent solution were confirmed by light microscopy and then placed in a quartz cuvette for spectroscopy. A portion of each cell sample was stained with Trypan Blue and the number of viable cells and total number of cells (cells per cubic millimeter) estimated using known microscopic techniques. The intensity of autofluorescence emitted from the samples was measured at 330 nm, with an excitation wavelength of 290 nm. The fluorescence intensity in each sample at 330 nm was divided by the estimated number of cells. The results from normal and malignant cells were then compared.

Figure 8:
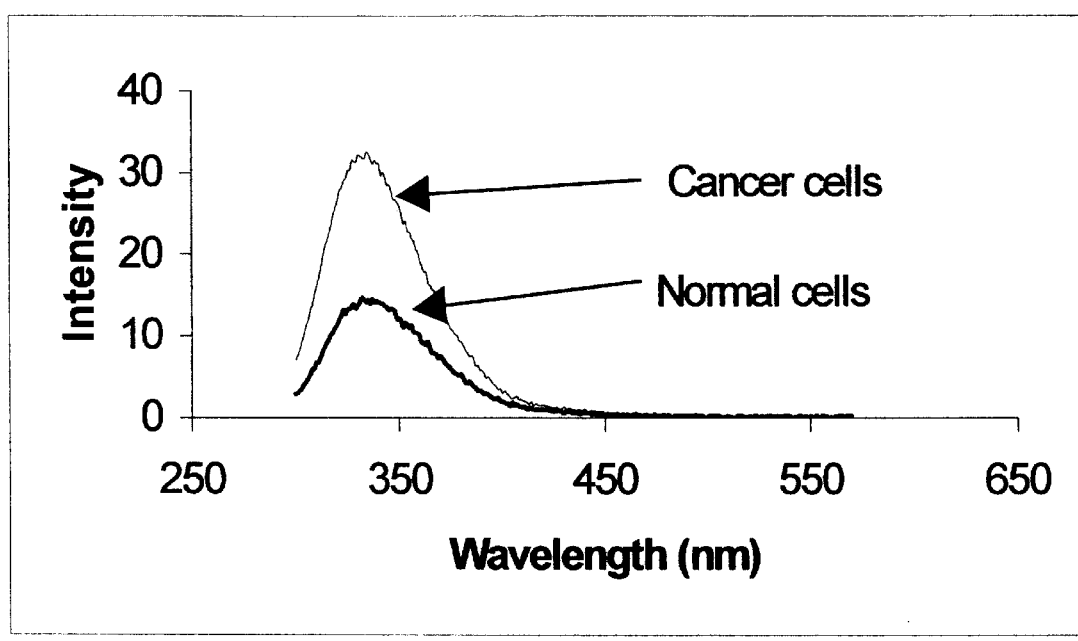
FIG. 8 shows emission spectra of normal colon cells and cancerous colon cells.

FIG. 8 shows the emission spectra of cells obtained from normal colon tissue (normal cells) and cells from adenocarcinoma of the colon (cancer cells). The spectra show the S peak for both cell types at about 330 nm. No other emission peaks were observed, and the spectra were identical to those obtained with the same excitation wavelength from cultured cells of the same type. FIG. 8 also shows that the intensity of the autofluorescence represented by the peak at about 330 nm in spectra of cancerous cells was substantially higher than that observed in the spectra of normal cells.

Table 2 shows the mean autofluorescence per cell in normal and malignant cells extracted from colon and esophagus. Table 2 shows that the mean autofluorescence per cell was greater in malignant cells than in normal cells.

TABLE 2

| Tissue | Mean autofluorescence per cell/mm³ | |
|---|---|---|
| | Colon | Esophagus |
| Normal | 4.5 | 4.9 |
| Malignant | 13.4 | 18.2 |
| Ratio:malignant/normal | 3 | 3.7 |

EXAMPLE 5

To investigate the effect of fixative on cellular autofluorescence, cells fixed in a solution of 10% formalin were studied. Specifically, cultured human colon adenocarcinoma cells (HT29-18N2) were grown on a coverslip and then fixed. Cells were then kept at room temperature in a closed box. Emission spectra were obtained at several post-fixation time points, at an excitation wavelength of 290 nm, and the peak autofluorescence intensity at about 330 nm was measured. Spectroscopy was performed at the following times after fixation: 50 minutes, 1 day, 8 days, 14 days and 75 days.

Table 3 shows the peak intensity at about 330 nm of the cultured cells, as measured at the different time periods after fixation. The results show cellular autofluorescence, and more specifically, the cellular Tryptophan-associated peak at about 330 nm is maintained for many days at room temperature after cells have been fixed in a standard fixative.

TABLE 3

| Time post fixation | Peak intensity at about 330 nm |
|---|---|
| Baseline (no formalin) | 5.3 |
| 50 min | 4.5 |
| 1 day | 6.4 |
| 8 days | 7.0 |
| 14 days | 5.8 |
| 75 days | 4.9 |

A similar experiment was performed on cells extracted from tissue. The cells were also fixed in a 10% formalin solution and spectroscopy performed as described above. Although the absolute intensities of the cellular Tryptophan-associated peak was changed, the difference in intensity between normal and malignant cells was maintained. Before fixation, the intensity of malignant cells at about 330 nm was 71% greater than that of normal cells. After fixation, the intensity of the same malignant cells was 125% greater than that of normal cells. Thus, it appears that fixation on formalin not only preserves the Tryptophan-associated autofluorescence, but for cell samples amplifies the difference in the autofluorescence intensity between normal and malignant cells. This suggests that the Tryptophan-associated autofluorescence can be used for automated cytology. For example, cell smears obtained from organs can be fixed in formalin and transported at room temperature to a facility where cellular autofluorescence is measured and a figure for autofluorescence per cell obtained.

EXAMPLE 6

To investigate the cellular source of the Tryptophan-associated autofluorescence, cells were separated from colonic tissue, homogenized and sonicated to rupture the cell wall, and centrifuged to produce a supernatant of cytosol and a membranous sample. The membranous sample was separated and dissolved, and then both the cytosolic supernatant and membranous sample were subjected to spectroscopy. The Tryptophan-associated peak at about 330 nm was observed in both fractions, but at much greater intensity in the membranous fraction.

Figure 9:
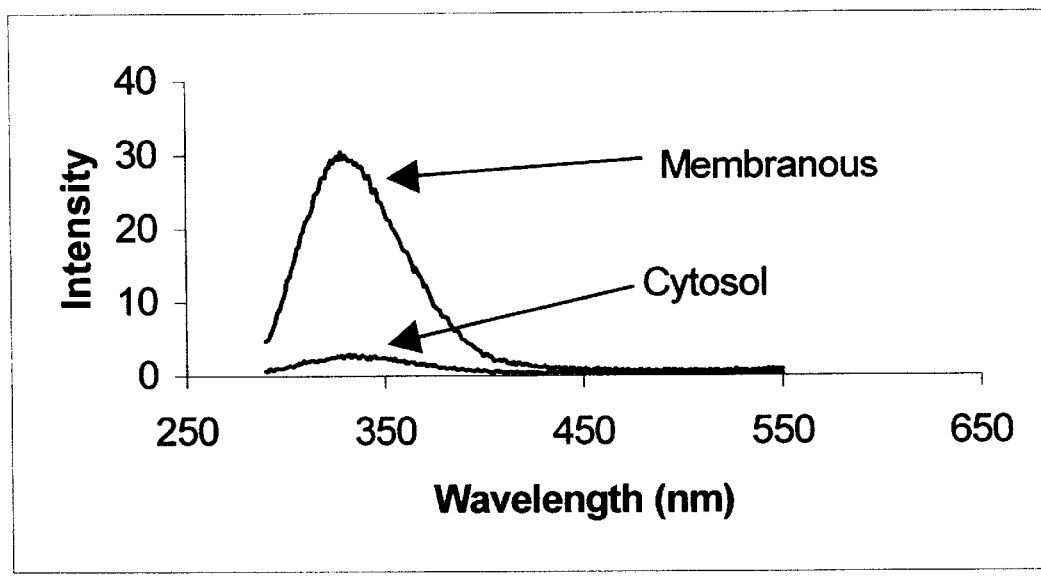
FIG. 9 shows emission spectra of membranous and cytosolic fractions derived from cells obtained from normal colonic tissue.

FIG. 9 shows the emission spectrum of membranous and cytosolic fractions derived from cells obtained from normal colonic tissue. The peak observed at about 330 nm is most likely due to Tryptophan as discussed in more detail above. Thus it appears that the Tryptophan-associated peak originates primarily from a source in the membranous constituents of cells. Such a source is likely to be a membrane-associated protein, group of proteins, or other Tryptophan-containing molecules. It is believed that the such a molecule or molecules is present in increased amounts in cancerous and pre-cancerous cells, thus accounting for the increase in intensity of the Tryptophan-associated autofluorescence in such cells.

This increase in cellular Tryptophan-associated autofluorescence is observable with excitation wavelengths from about 200 nm to about 400 nm. However, excitation with light having a wavelength from about 280 nm to about 300 nm is especially suitable. At excitation wavelengths outside of the range of 280 nm to 300 nm, for example with excitation at 310 nm to 320 nm, other emission peaks appear in addition to the cellular Tryptophan-associated peak at about 330 nm, although the peak is still detectable and allows intensity measurements to be made. Even when whole tissue is studied with a suitable excitation wavelength, only autofluorescence from the cells within the tissue is observed. This creates a selective optical window through which cellular autofluoresence can be observed without interference from extracellular fluorophores. The increase in cellular Tryptophan-associated autofluorescence with a peak at about 330 nm, observed with excitation in the wavelength range of about 230 nm to about 350, is thus distinguishable from a reported decrease in tissue autofluorescence in malignant tissue, with excitation in the same wavelength range, at an emission wavelength of about 450 nm to 460 nm.

EXAMPLE 7

To demonstrate that single intensity measurements of the cellular Tryptophan-associated peak at about 330 nm can identify dysplasia and cancer of the esophagus, tissue samples were obtained from the esophagus, stomach, colon and small intestine. Normal, pre-malignant (dysplastic), malignant and inflamed tissue samples were obtained and the intensity of the Tryptophan-associated peak at about 330 nm measured using an excitation wavelength of 290 nm. A normalized intensity ratio of diseased tissue over normal tissue, (where normal tissue was assigned an intensity value of 1), was then calculated.

Figure 10:
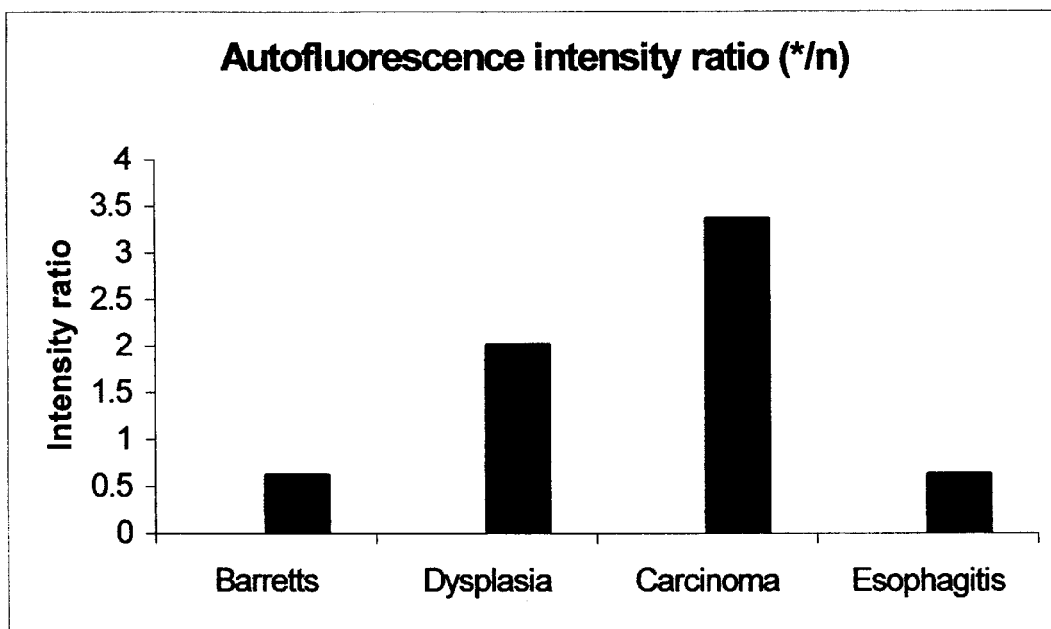
FIG. 10 shows autofluorescence ratios of a Tryptophan-associated emission peak for different types of esophageal tissue.

Table 4 shows the mean intensity ratio for esophageal tissue±the standard error of the mean (SE). FIG. 10 shows the autofluorescence ratio of the Tryptophan-associated peak for the different types of esophageal tissue studied. Barrett's esophagus is an intestinal metaplasia with a potential for malignant transformation. Esophagitis is an inflammatory condition. Dysplasia, an abnormal sate that progresses to malignancy, and carcinoma are neoplastic conditions of increasing malignancy. The results indicate that inflammation does not enhance, but instead slightly reduces cellular autofluorescence at about 330 nm. In contrast, the intensity ratio increases for low grade dysplasia and carcinoma. Thus, the single intensity measurement distinguishes inflamed tissue and Barrett's metaplasia (with a reduction in the intensity ratio), and dysplastic and malignant tissue (with an increase in the intensity ratio) from normal tissue. This will avoid false positive results during cancer surveillance in patients with inflammatory conditions.

TABLE 4

| Diagnosis (*) | Number | Intensity ratio: */normal ± SE |
|---|---|---|
| Barrett's (intestinal metaplasia) | 17 | 0.62 ± 0.67 |
| Dysplasia (low grade) | 8 | 2.01 ± 0.29 |
| Carcinoma | 7 | 3.36 ± 1.03 |
| Esophagitis (inflammation) | 4 | 0.63 ± 0.06 |

Figure 11:
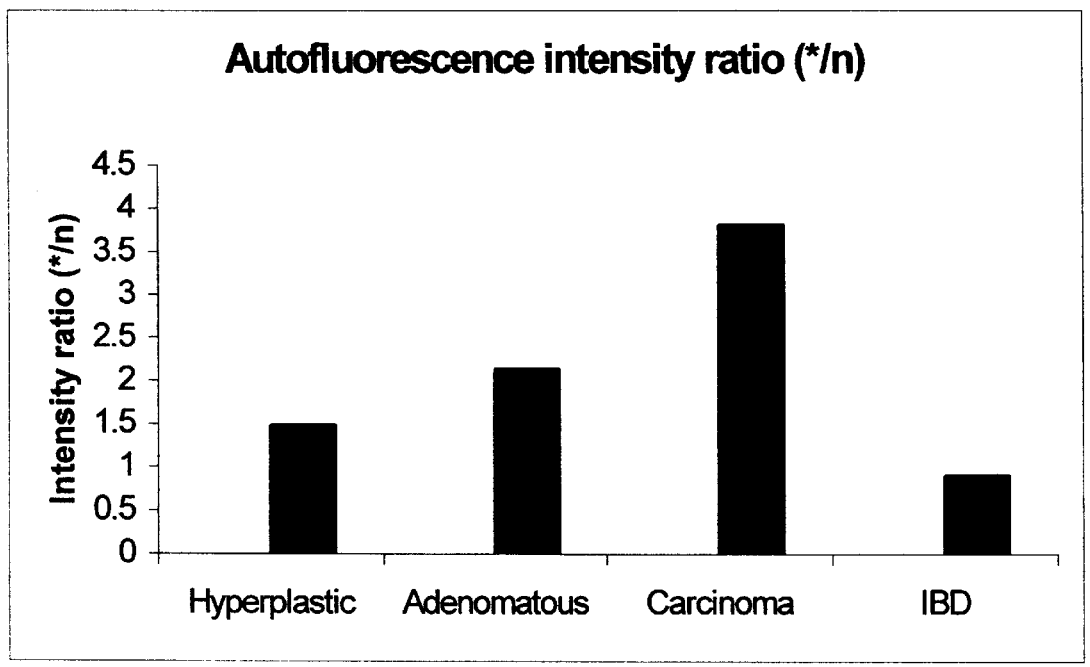
FIG. 11 shows autofluorescence ratios of the Tryptophan-associated peak for different types of colonic tissue studied.

Table 5 shows the mean intensity ratio for colonic tissue±the standard error of the mean (SE). FIG. 11 shows the autofluorescence ratio of the Tryptophan-associated peak for the different types of colonic tissue studied. Hyperplastic polyps are growths lacking malignant potential. They are polyploid, but contain normal cells. Adenomatous polyps are benign growths with malignant potential and include cells which are "atypical". If detected, adenomatous polyps should be removed, but they are not cancerous. However, if left unremoved, adenomatous polyps can develop into cancer. Inflammatory Bowel Disease (IBD), including Ulcerative Colitis and Crohn's Disease, are chronic inflammatory conditions with an increased risk of cancer.

Referring to Table 5, the results indicate that inflammation (IBD) does not enhance, but instead slightly reduces cellular autofluorescence intensity at about 330 nm, similar to the results obtained with inflamed esophageal tissue as described above. In contrast, the intensity ratio is higher for hyperplastic tissue than for normal mucosa. The ratio increases stepwise for adenomas and cancer. Thus, the single intensity measurement distinguishes inflamed colonic tissue (with a reduction in the intensity ratio), and hyperplastic, dysplastic and malignant tissue (with an increase in the intensity ratio) from normal tissue. This will avoid false positive results during cancer surveillance in patients with IBD.

TABLE 5

| Diagnosis (*) | Number | Intensity ratio: */normal ± SE |
|---|---|---|
| Hyperplastic | 9 | 1.48 ± 0.16 |
| Adenomatous | 22 | 2.13 ± 0.16 |
| Carcinoma | 11 | 3.81 ± 0.71 |
| IBD | 15 | 0.9 ± 0.04 |

The use of excitation scans to detect cancer was also investigated. In excitation scans, as opposed to the emission scans described above, the emission wavelength is kept constant and the excitation wavelength varied. The excitation scans for Tryptophan, cultured cells, and cells extracted from tissue all reveal a major excitation peak at 290 nm. This peak is also observed in whole tissue, and reveals the presence of cancer in a manner similar. to that using emission scans as described above.

Specifically, excitation spectra of normal, dysplastic and cancerous and esophageal tissue were obtained by varying the excitation wavelength from 220 nm to 340 nm. A single intensity measurement of the major Tryptophan-associated excitation peak was taken at 290 nm for each tissue type. The mean intensity measurement for each tissue type was normalized to the intensity measurement for normal tissue at 290 nm (mean intensity=1). The ratios of mean emission intensities were: 1.42±0.35 (SE) for low grade dysplasia of Barrett's, (N=6); and 4.03±1.17 for adenocarcinoma (N=9). Thus, the results indicate that single intensity measurements of cellular Tryptophan-associated excitation spectra distinguishes cancerous tissue from dysplastic and normal tissue.

The methods thus embody the first application of cell-specific autofluorescence in the tissue diagnosis of malignancy. When whole tissue is excited at a wavelength in the range of about 230 nm to about 350 nm, for example at about 290 nm, the autofluorescence emitted from the tissue and measured at an emission wavelength of about 330 nm comes predominantly from cells, and is most likely due to the amino acid Tryptophan. The intensity of cellular Tryptophan-associated autofluorescence is distinguishable in normal, pre-cancerous, and cancerous cells, increasing with an increase in malignancy. The methods use the Tryptophan-associated cellular autofluorescence to detect the specifically cellular changes indicative of cancer and early cancer. The methods employ the optical techniques of obtaining either excitation spectra or emission spectra of tissue or cell samples to reveal the change in cellular Tryptophan-associated autofluorescence which is indicative of early cancer or cancer. The methods have the clear advantage of involving only a single intensity measurement from a peak in a spectrum, instead of multiple point analysis of a complex waveform. Further, the methods provide rapid optical detection of malignancy.

Cellular Tryptophan-associated autofluorescence is not affected by the presence of inflammatory conditions in the same way as it is affected by the presence of malignancy. Inflammation causes a decrease in cellular Tryptophan-associated autofluorescence. Therefore, when screening for cancer in patients with inflammatory conditions, a decreased risk exists of obtaining false positive results due to the inflamed tissue in such patients.

In alternative embodiments of the method, whole multiples of the excitation wavelengths are used to obtain the same cellular, Tryptophan-associated autofluorescence with multi-photon excitation. The multi-photon excitation approach is especially suitable for penetrating deep tissue, but is also suitable for examining surface tissue. To obtain emission spectra using multi-photon excitation, pulsed excitation at multiples of 290 nm, or an other suitable excitation wavelength in the range of about 200 nm to about 400 nm as described above, can be used. For example, to penetrate deep tissue, two photon pulsed excitation at 580 nm, or three photon pulsed excitation at 870 nm is used to obtain the same cellular, Tryptophan-associated autofluorescence.

The methods are applicable to cell or tissue samples from a wide range of organs. For example, the methods are applicable to direct examination of organs such as skin, or by using two way optic fiber probes passed through endoscopes to examine internal organs such as the esophagus, stomach, colon, lung, bladder, cervix, bile and pancreatic ducts. Breast tissue and other solid organs are accessible to the method by passing a fiber optic bundle through a needle or trocar. Alternatively, deep tissue or sub-surface spectroscopy is accomplished with the methods using multi-photon excitation.

Further, the method is useful for defining a safe margin in real time as a malignancy is being resected by a surgeon, thus avoiding the need for frozen sections to be examined by a pathologist during the surgery as is typically done. The methods are also applicable to automated cell measurements, or cytometry, wherein cell samples of normal or suspected malignant tissue, obtained via tissue brushings, smears or fluid aspirations, are examined, fixed or unfixed, in an automated cytometer for the Tryptophan-associated autofluorescence. Thus, any tissue sample being used to practice the method can be a cytological sample obtained through such cytological sampling methods.

Still further, the methods are suitable for use in combination with the use of known dyes, stains and contrast agents because the cellular, Tryptophan-associated autofluorescence peak remains unaffected by such agents. These agents include, for example, methylene blue and other dyes or stains commonly used by physicians as contrast agents during, for example, endoscopy procedures or the like. The contrast agents help locate probable areas of pathology. In addition, the methods described herein are consistent with the use of exogenous dyes and fluorescent agents, which also do not affect the Tryptophan-associated autofluorescence peak. Therefore, alternative embodiments of the method include the step of applying a suitable contrast agent to a sample of tissue or tissue site to be examined, and then using the contrast agent to identify likely areas of pathology which are then further examined for Tryptophan-associated autofluorescence.

Even further, a charge-coupled device (CCD) can be used in combination with the methods to construct visual images of tissue being examined, wherein the intensity measurements are calibrated to, for example, a color coded scale and displayed on a video monitor. Such an application of the methods allows simultaneous scanning of large areas of tissue.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for detection of cancerous cells, said method comprising:

(a) exposing cells from a tissue of a patient and which are suspected of being cancerous to a light beam;

(b) measuring one intensity of autofluorescence emission from the cells wherein said autofluorescence emission measurement is limited to a wavelength or band of wavelengths between 320 nm and 340 nm; and (c) determining whether the cells are cancerous, wherein said determining consists of concluding that the cells are cancerous if the one intensity of autofluorescence emission is greater than that of non-cancerous cells from the same patient and of the same tissue type as the cells suspected of being cancerous.

2. The method of claim 1 wherein the measuring of autofluorescence emission measures cell specific fluorescence and excludes extracellular fluorescence.

3. The method of claim 2 wherein the measuring of autofluorescence emission measures cell specific fluorescence originating from tryptophan.

4. The method of claim 1 wherein the wavelength or band of wavelengths is a wavelength of about 330 nm.

5. The method of claim 4 wherein the light beam to which the cells are exposed is limited to wavelengths between about 270–310 nm.

6. The method of claim 1 further comprising determining a ratio of intensity of cellular autofluorescence of the cells suspected of being cancerous to intensity of autofluorescence in cells which are not cancerous.

7. The method of claim 6 further comprising assessing severity of cancer progression as a function of the determined ratio, wherein a greater ratio indicates more severity of degree of cancer.

8. The method of claim 1 wherein the cells are in vivo.

9. The method of claim 8 wherein exposing the cells to light comprises exposing the cells to a beam of ultraviolet light delivered through a two-way fiber optic bundle in an endoscope or in a needle.

10. The method of claim 1 wherein the cells are in vitro.

11. The method of claim 1 wherein the cells suspected of being cancerous are from skin or an esophagus, stomach, colon, lung, bladder, cervix, bile, pancreatic duct, or from breast tissue.

* * * * *